Feb. 7, 1961 G. A. REID Plant Pat. 2,021
AZALEA PLANT
Filed March 17, 1960
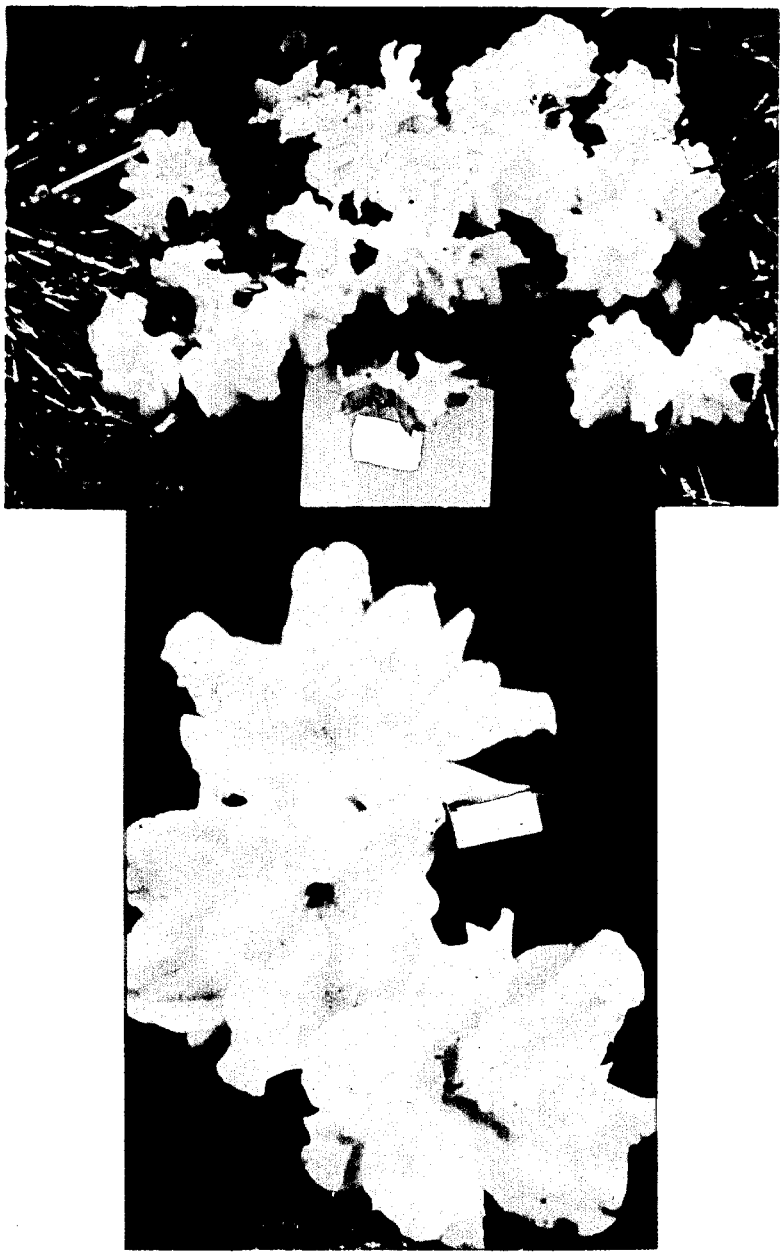
INVENTOR
George Albert Reid
BY Robb & Robb
ATTORNEYS United States Patent Office Plant Pat. 2,021
Patented Feb. 7, 1961

2,021

AZALEA PLANT

George Albert Reid, Linwood, N.J., assignor to Fischer Greenhouses, Linwood, N.J., a corporation of New Jersey Filed Mar. 17, 1960, Ser. No. 15,777
1 Claim. (Cl. 47—60)

The present invention relates to a new and distinct variety of azalea plant of a type which combines many of the desirable characteristics of both the Indian and Kurume forms of azalea varieties, said new variety having been originated by me by crossing two unnamed and unpatented varieties.

My new variety, referred to above, resulted from an extensive breeding program which I carried out in an effort to develop new azalea varieties having improved characteristics, particularly from the standpoint of both flower color and winter-hardiness of the plants and flowers. The new variety is one of those which was achieved by this breeding program. So far as I am aware, Indian type azaleas have never before been available in a hardy form, and as a general rule, bright flower colors and large and complicated flower forms have heretofore been found only in the tender azaleas which cannot withstand low temperatures.

As the result of the breeding of the present new variety, I have achieved desirable improvements from the standpoint of attractiveness, as well as from the standpoint of important commercial advantages, as evidenced from the following unique combination of outstanding characteristics which differentiate my new variety from all other azalea varieties of which I am aware:

(1) Extremely good winter-hardiness of both the plant and buds (has withstood temperatures as low as −5° F. without injury);

(2) An evergreen habit;

(3) Large flower size;

(4) Interesting and complicated, semi-double, hose-in-hose flower form;

(5) Bright, Strong Purplish Red general color tonality of the flowers; and (6) Suitability for early greenhouse forcing, with a blooming range running from the latter part of December to approximately mid-May.

Asexual reproduction of my new variety as performed by cuttings, at Linwood, New Jersey, shows that the foregoing characteristics and distinctions come true to form and are established and transmitted through succeeding propagations.

The accompanying drawing shows a typical specimen plant of my new variety, as well as typical specimen blooms on an enlarged scale, as depicted in color as nearly true as it is reasonably possible to make the same in a color illustration of this character.

The following is a detailed description of my new azalea variety, with color terminology in accordance with Nickerson Color Fan, published by Munsell Color Company, Inc., of Baltimore, Maryland, except where general color terms of ordinary dictionary significance are obvious, and as based upon observations made from specimens grown in a greenhouse at Linwood, New Jersey:

Propagation: Holds its distinguishing characteristics through succeeding propagations by cuttings.

*Plant*

Form: Bush; much-branched; compact.
Habit: Medium vigorous.
Foliage:
*Size.*—Medium.
*Quantity.*—Normal.
*Color.*—New foliage: upper side—Moderate Yellow Green, Plate 5GY 5/6; under side—Brilliant Yellow Green, Plate 5GY 8/8. Old foliage: upper side—Moderate Olive Green, Plate 7.5GY 4/4; under side—Moderate Yellow Green, Plate 5GY 5/6.
*Shape.*—Oval pointed.
*Texture.*—Upper side—leathery. Under side—rough.
*Margin.*—Shape—smooth edge.
*Aspect.*—Generally resembles Kurume type foliage.
*Disease resistance.*—Excellent, as evidenced by the fact that no diseases of foliage or flower have appeared over a period of several years as compared with other varieties grown under the same cultural conditions in the same locality at Linwood, New Jersey, and no problems have been presented by common propagation stage diseases, as evidenced by the fact that the new variety achieves almost perfect rooting under diverse conditions.

*Flowers*

Borne: Several to stem; in irregular rounded clusters; on strong, short stems.
Quantity of bloom: Free, both outdoors and in greenhouse.
Continuity: One season. Permanence—blooms are retained better-than-average, and keeping quality both indoors and outdoors is better-than-average.
Size: Large; about 2¼ iches in diameter.
Petalage: Semi-double; hose-in-hose.
*Number of petals under normal conditions.*—From 12 to 15 petals, arranged in two whorls of 5 petals each, with a center whorl of from 2 to 5 staminoid petals.
*Color.*—Strong Purplish Red, Plate 10RP 5/12.
*Texture.*—Smooth.
*Appearance.*—Inside—Strong Purplish Red, Plate 10RP 5/12. Outside—slightly lighter than Strong Purplish Red, Plate 10RP 5/12.
*Shape.*—Petals are waved and slightly fringed.
*General color tonality.*—Strong Purplish Red, Plate 10RP 5/12.
Bud: Color—Strong Purplish Red, Plate 10RP 5/12.

*Reproductive organs*

Stamens: Color—pink.
Pollen: Color—white.
Styles: Color—pink.
Ovaries: Color—pink.
General Observations: My new variety represents a combination of desirable color, size and form of the Pericats and Indian types, together with the winter-hardiness and evergreen characteristics of Kurume and Kaempferi types. Its flowers are nearest in color and form to the Indian variety "Early Wonder" (unpatented), but they are slightly smaller and less double than the flowers of that variety. The plant habit most nearly resembles that of the Pericat variety "Pericat Salmon" (unpatented).

I claim:

A new and distinct variety of azalea plant, substantially as herein shown and described, characterized particularly as to novelty by the unique combination of extremely good winter-hardiness of both the plant and buds, an evergreen habit, large flower size, an interesting and complicated semi-double hose-in-hose flower form, a bright, Strong Purplish Red general color tonality of the flowers, and a suitability for early greenhouse forcing, with a general blooming range extending from the latter part of December to approximately mid-May.

No references cited.